(12) United States Patent
Araki et al.

(10) Patent No.: US 8,105,294 B2
(45) Date of Patent: Jan. 31, 2012

(54) SYRINGE AND SYRINGE BARREL

(75) Inventors: Masaya Araki, Tokyo (JP); Hideaki Kawamura, Tokyo (JP)

(73) Assignee: Daikyo Seiko Ltd., Tokyo (JP)

( * ) Notice: Subject to any disclaimer, the term of this patent is extended or adjusted under 35 U.S.C. 154(b) by 0 days.

(21) Appl. No.: 12/740,878

(22) PCT Filed: Aug. 30, 2008

(86) PCT No.: PCT/JP2008/065604
§ 371 (c)(1),
(2), (4) Date: Jul. 22, 2010

(87) PCT Pub. No.: WO2009/057378
PCT Pub. Date: May 7, 2009

(65) Prior Publication Data
US 2010/0305513 A1 Dec. 2, 2010

(30) Foreign Application Priority Data

Oct. 31, 2007 (JP) .................. 2007-284563

(51) Int. Cl.
*A61M 5/00* (2006.01)
(52) U.S. Cl. .................. 604/207; 604/181; 604/187

(58) Field of Classification Search .................. 604/187, 604/218, 181, 207, 208, 93.01, 110
See application file for complete search history.

(56) References Cited

U.S. PATENT DOCUMENTS

| 4,995,869 A * | 2/1991 | McCarthy | 604/110 |
| 5,047,017 A * | 9/1991 | Koska | 604/110 |
| 5,106,372 A * | 4/1992 | Ranford | 604/110 |
| 6,972,006 B2 * | 12/2005 | Ferguson | 604/208 |

* cited by examiner

*Primary Examiner* — Kevin C Sirmons
*Assistant Examiner* — Laura Schell
(74) *Attorney, Agent, or Firm* — Kile Park Goekjian Reed & McManus PLLC (57) ABSTRACT

To provide a syringe barrel and a syringe capable of allowing an operator to feel the amount of injected medical solution or the inserting distance of a piston by a difference in sliding resistance when an injection operation is performed. A syringe 1 includes a syringe barrel 11 which has an inner surface provided with a structure in which a sliding resistance F is changed step by step upon sliding a piston 32. The syringe barrel 11 includes steps which are formed at one or two or more positions of the inner surface in the axial direction so as to face from the rear end to the front end or from the front end to the rear end, and which include edges formed along the circumferential direction.

9 Claims, 10 Drawing Sheets

SYRINGE AND SYRINGE BARREL

TECHNICAL FIELD

The present invention relates to a syringe and a syringe barrel capable of allowing a doctor, etc. to feel the amount of injected medical solution or the inserting distance of a piston by a difference in sliding resistance when an injection operation is performed.

BACKGROUND ART

Figure 10:
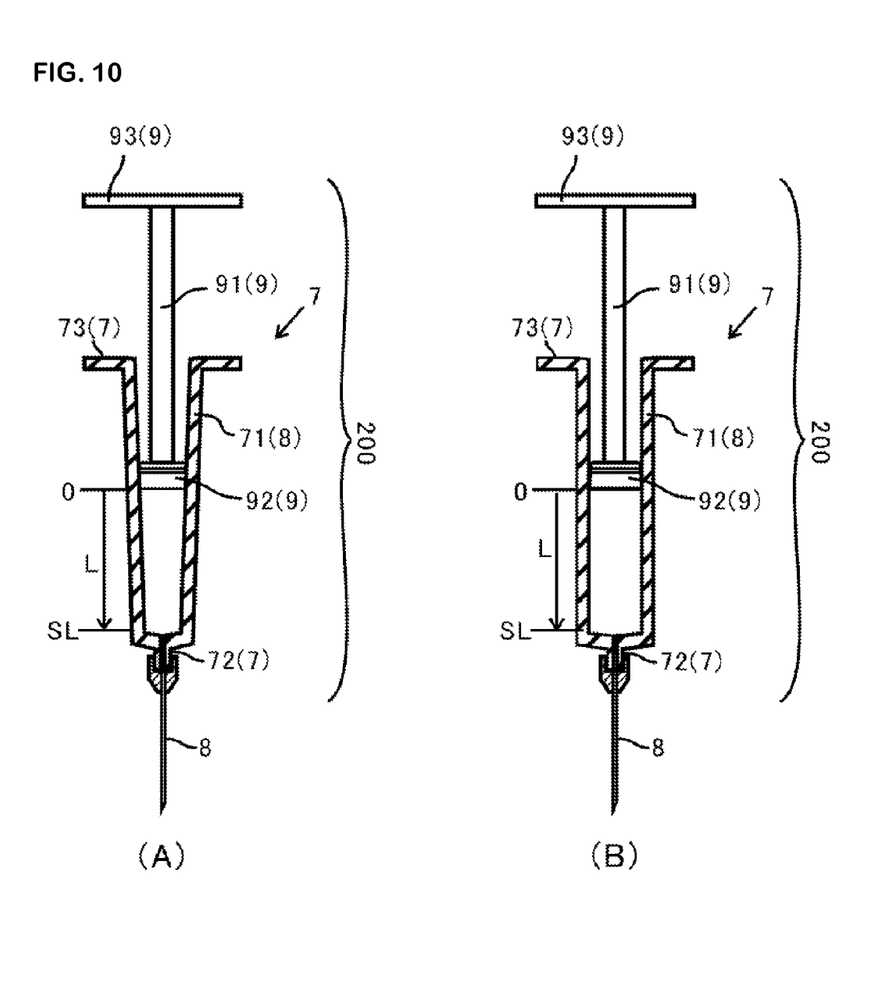
FIG. 10 is a cross-sectional explanatory diagram showing the syringe of the background art, where

FIGS. 10(A) and 10(B) are cross-sectional explanatory diagrams showing a syringe of a background art, where FIG. 10(A) is a diagram showing a syringe having a narrowed tip, and FIG. 10(B) is a diagram showing a syringe having a uniform inner diameter.

A syringe 200 of FIGS. 10(A) and 10(B) is manufactured by injection molding, and includes a syringe barrel 7, a needle 8, and a piston set 9 (including a piston rod 91, a piston 92, and an operational flange 93).

In FIGS. 10(A) and 10(B), for convenience of description, the characteristics of the syringe 200 are exaggerated. For example, in the syringe 200 of FIGS. 10(A) and 10(B), the thickness of the syringe barrel 7 and the size of the needle 8 are different from those of the actual syringe. In addition, for example, in the syringe 200 of FIG. 10(A), it is depicted that the shape in which the tip of the inner outline of the syringe barrel 7 is narrow (the taper of the inner outline in the axial direction is magnified) is visibly recognized. However, in the actual syringe 200, the shape in which the tip of the inner outline of the syringe barrel 7 is narrow cannot be visibly recognized.

DISCLOSURE OF THE INVENTION

Problems that the Invention is to Solve

Therefore, in the syringe 200 of the background art, in the case where a part (for example, ½, ⅓, etc. of the total amount) of medical solution inside the syringe barrel 7 is injected, if gradations are marked on the side surface of the syringe barrel 7, the piston 92 is slid by using the gradations as a target.

However, in the environment, etc. of the injection operation, there is a case in which the gradations cannot be accurately used as a target. In addition, even in the case where the gradations can be accurately seen, there is a case in which a patient's face needs to be carefully watched.

An object of the invention is to provide a syringe barrel and a syringe capable of allowing a doctor, etc. to feel the amount of injected medical solution or the inserting distance of a piston by a difference in sliding resistance when an injection operation is performed.

Means for Solving the Problem

A syringe of the invention has Aspect (1).

(1) A syringe including: a syringe barrel which includes an inner surface provided with a structure in which a sliding resistance is changed step by step upon sliding a piston.

For example, the inner surface of the syringe barrel or the piston may be provided with a structure in which the sliding resistance increases by 1.5 to 3 times upon sliding the piston at a speed of 100 mm/min in the case where an injection operation is performed (the case where a needle is attached to a nozzle of the syringe barrel, water is filled into the syringe barrel, and then piston is pressed and slid).

A syringe barrel of the invention has Aspects (2) to (7).

(2) A syringe barrel including: steps which are formed at one or two or more positions of an inner surface of the syringe barrel so as to uprightly formed from the rear end to the front end or from the front end to the rear end in the axial direction, and include edges along the circumferential direction.

The "front end" of the syringe barrel is the end on the side provided with the nozzle, and the "rear end" is the end on the opposite side thereof.

(3) The syringe barrel according to (2), wherein the steps are formed in an annular shape (generally the steps are continuously formed throughout the circumference, but may be intermittently formed) along the circumferential direction.

(4) The syringe barrel according to (2) or (3), wherein the capacity is 20 mL or less (desirably, 5 mL or less).

For example, in the case where an injection operation is performed (the case where a needle is attached to a nozzle of the syringe barrel, water is filled into the syringe barrel, and then piston is pressed and slid), the sliding resistance upon passing through the steps at a speed of 100 mm/min may be set to be larger by 1.5 to 3 times than the sliding resistance immediately before passing through the steps.

In addition, in the syringe barrel of (2) to (4) including the plurality of steps, the diameter of the edge of the rear end side step may be set to be equal to the diameter of the edge of the front end side step, and may be set to be larger than the diameter of the edge of the front end side step.

(5) A syringe barrel including: concave portions or convex portions which are formed in the circumferential direction at one or two or more positions of an inner surface of the syringe barrel in the axial direction.

(6) The syringe barrel according to (5), wherein the concave portions or the convex portions are formed in an annular shape (generally the concave portions and the convex portions are continuously formed throughout the circumference, but may be intermittently formed) along the circumferential direction.

(7) The syringe barrel according to (5) or (6), wherein the capacity is 20 mL or less (desirably, 5 mL or less).

For example, in the case where an injection operation is performed (the case where a needle is attached to a nozzle of the syringe barrel, water is filled into the syringe barrel, and then piston is pressed and slid), the sliding resistance upon passing through the concave portions or the convex portions at a speed of 100 mm/min may be set to be larger by 1.5 to 3 times than the sliding resistance immediately before passing through the concave portions or the convex portions.

Advantage of the Invention

According to the invention, a doctor, etc. can recognize the amount of injected medical solution or the inserting distance of a piston by feeling a difference in sliding resistance upon performing an injection operation. Therefore, for example, even under the environment in which nothing can be visibly recognized, the amount of injected medical solution can be recognized, and the injection operation can be performed by using the amount of ½, ⅓, etc. of the amount of filled medical solution.

In addition, since the steps or the uneven portions formed on the inner surface of the syringe barrel can be visibly recognized from the outside, they may be used as gradations.

Further, when the injection operation is completed when the sliding resistance of the piston increases, the injection operation can be performed by an accurate amount.

BRIEF DESCRIPTION OF THE DRAWINGS

FIG. 1(A) is a cross-sectional explanatory diagram of the syringe, FIG. 1(B) is an enlarged cross-sectional view of the vicinity of a piston of the syringe barrel, and FIG. 1(C) is an enlarged view of the vicinity of the front end side step among two steps of the syringe barrel.

FIG. 3(A) is a diagram showing a shape before injection molding, and FIG. 3(B) is a diagram showing a shape in which an inner mold is inserted into an outer mold.

FIG. 4(A) is a diagram showing a shape in which an inner mold is extracted together with a molded syringe barrel, and FIG. 4(B) is a diagram showing a shape in which the syringe barrel is separated from the inner mold.

FIG. 5(A) is a cross-sectional explanatory diagram of the syringe, FIG. 5(B) is an enlarged cross-sectional view of the vicinity of the piston of the syringe barrel, and FIG. 5(C) is an enlarged view of the vicinity of the front end side step among two steps of the syringe barrel.

FIG. 7(A) is a cross-sectional view of the syringe, FIG. 7(B) is an enlarged cross-sectional view of the vicinity of a piston of the syringe barrel, and FIG. 7(C) is an enlarged view of the vicinity of a front end side convex portion among two convex portions of the syringe barrel.

FIG. 8(A) is a cross-sectional explanatory diagram of the syringe, FIG. 8(B) is an enlarged cross-sectional view of the vicinity of the piston of the syringe barrel, and FIG. 8(C) is an enlarged view of the vicinity of the front end side convex portion among two convex portions of the syringe barrel.

FIG. 10(A) is a diagram showing the syringe having a narrowed tip, and FIG. 10(B) is a diagram showing the syringe having a uniform inner diameter.

DESCRIPTION OF REFERENCE NUMERALS AND SIGNS 1, 200: SYRINGE
2, 8: NEEDLE
3, 9: PISTON SET
7, 11: SYRINGE BARREL
10A, 10B, 10C, 10D: SYRINGE
12: NOZZLE
13: FLANGE
31, 91: ROD
32, 92: PISTON
33, 93: OPERATIONAL FLANGE
322: FRONT END SIDE CORNER
$S_1$, $S_2$: STEP/EDGE
$CB_1$, $CB_2$: CONVEX PORTION

BEST MODE FOR CARRYING OUT THE INVENTION

Hereinafter, embodiments of the invention will be described with reference to the drawings. In the below embodiments, a single-chamber syringe barrel is described, but the invention may be applied to a multi-chamber syringe barrel.

In the drawings, the characteristics of a syringe are exaggerated for convenience of description, but the actual outline, etc. are different. In addition, in the drawings, the syringe barrel is depicted to be relatively short and bold, but the actual syringe barrel generally has a thin body.

Figure 3:
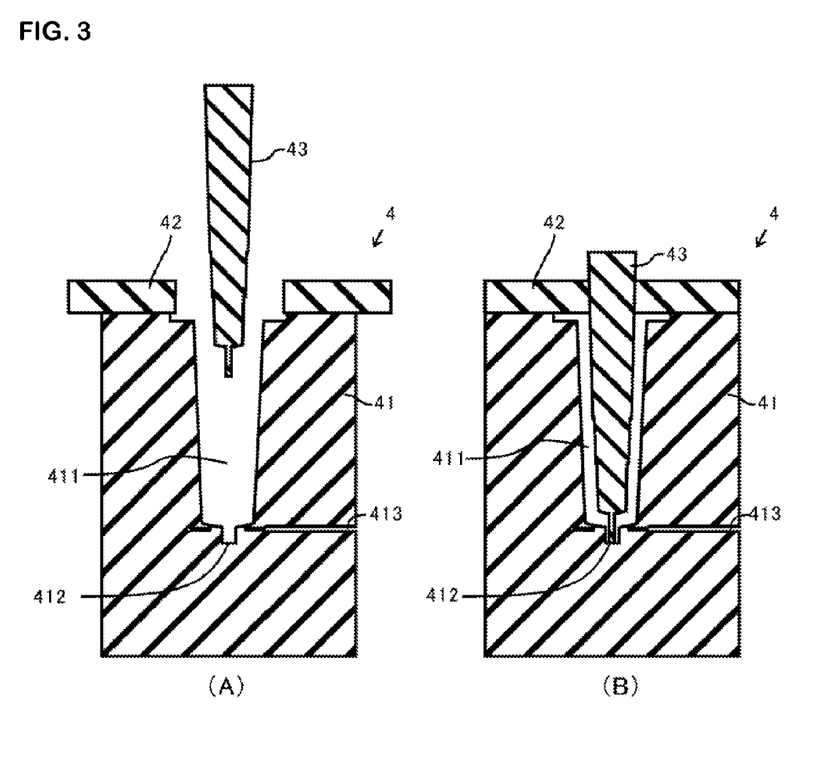
FIG. 3 is an explanatory diagram showing an injection molding machine used in the manufacture of the syringe barrel shown in FIG. 1, where
Figure 4:
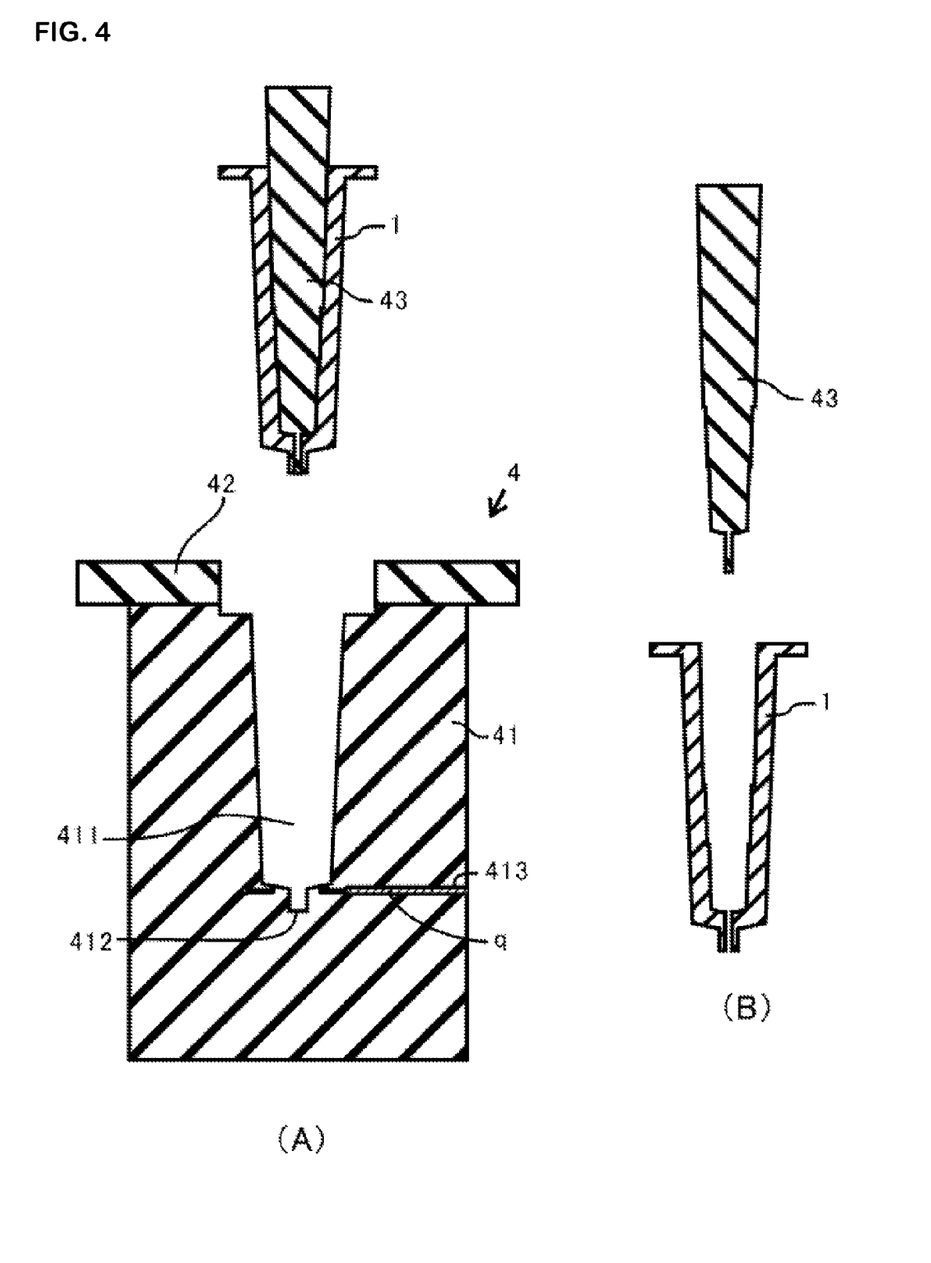
FIG. 4 is an explanatory diagram showing an injection molding machine used in the manufacture of the syringe barrel shown in FIG. 1, where
Figure 7:
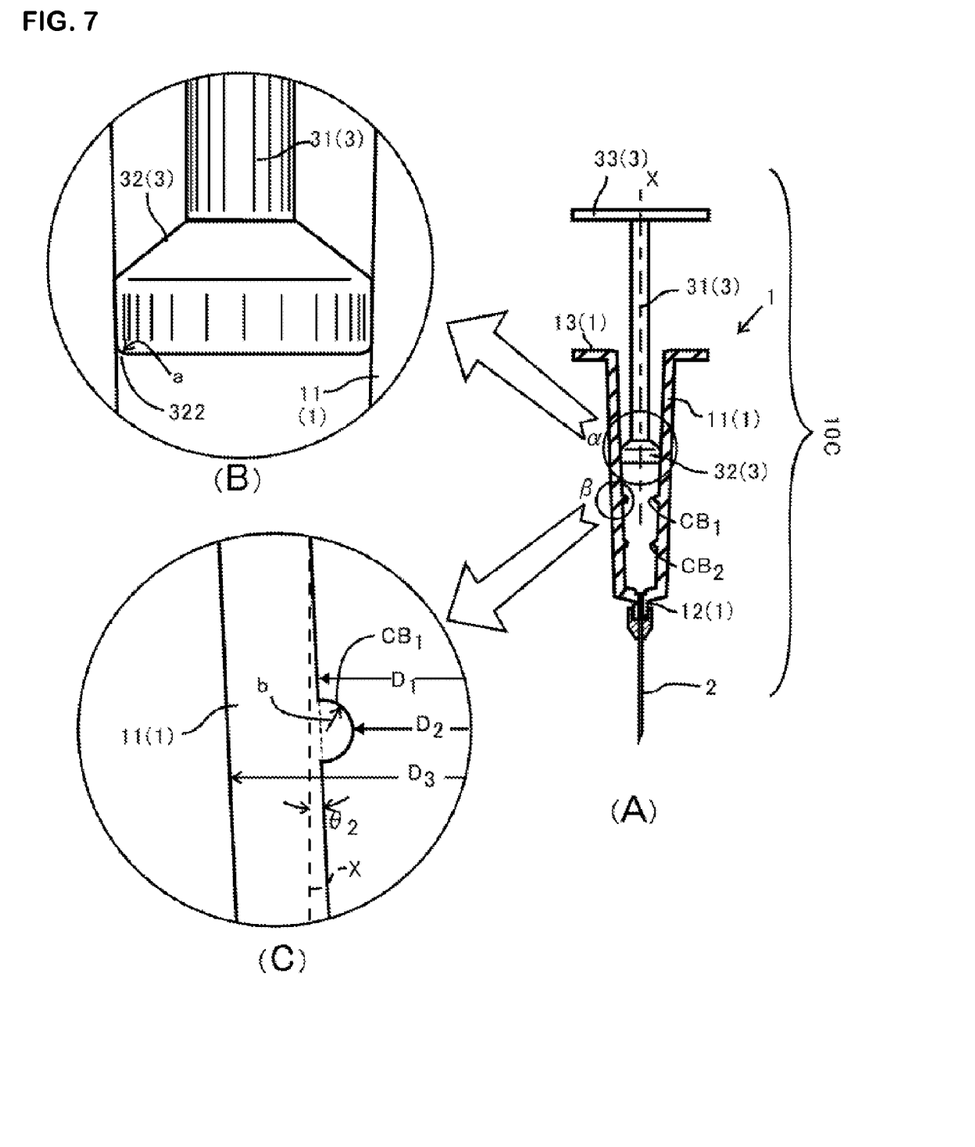
FIG. 7 is an explanatory diagram of an embodiment of a syringe barrel of the invention provided with an uneven portion and an embodiment of a syringe of the invention using the syringe barrel, where

In the example to be shown later (e.g., refer to FIG. 1 or 7), the tip of the outline of the inner space of the syringe barrel is narrow, and the shape is exaggerated to be visually recognized (the axial taper of the inner outline is largely shown). However, in the actual syringe, generally the shape, in which the tip of the inner outline or the outer outline of the syringe is narrow, cannot be visually recognized since the degree of the narrowed tip is minute. In addition, even in an injection molding machine described in FIGS. 3 and 4, generally, the shape of the narrowed tip of the outer outline of an inner mold and the inner outline of a cavity of an outer mold cannot be visually recognized.

FIGS. 1(A), 1(B), and 1(C) are explanatory diagrams of an embodiment of a syringe barrel of the invention provided with steps and an embodiment of a syringe of the invention using the syringe barrel.

As shown in FIG. 1(A), a syringe 10A includes a syringe barrel 1, a needle 2, and a piston set 3. In the syringe barrel 1, the front end thereof is provided with a nozzle 12, and the rear end thereof is provided with a flange 13. The piston set 3 includes a rod 31, a piston 32, and an operational flange 33. FIG. 1(B) shows an enlarged view of the vicinity α of the piston 32 of the syringe barrel 1, and FIG. 1(C) shows an enlarged view of the vicinity β of $S_1$ among two steps ($S_1$ and $S_2$) of the syringe barrel 1. In FIGS. 1(B) and 1(C), the hatching of the syringe barrel 1 is omitted for convenience of description.

The needle 2 (including a stainless needle portion and a synthetic resin attachment portion) is attached to the nozzle 12 of the syringe barrel 1. In addition, the piston 32 is attached to the front end of the rod 31, and is inserted into the syringe barrel 11 from the rear end thereof. In addition, the operational flange 33 is attached to the rear end of the rod 31.

In the embodiment, the syringe barrel 11 is formed of materials generally used for the syringe barrel, and examples of the materials include polypropylene, polymethylpentene, polyolefin such as cyclic polyolefin, polyethylene terephthalate, polyethylene naphthalate, noncrystalline polyarylate, etc.

Annular steps $S_1$ and $S_2$ are provided at two positions in the axial X direction of the inner surface of the syringe barrel 11, which are uprightly formed toward the front end (the downside in FIG. 1(A)) and each of which includes an edge along the circumferential direction. In the embodiment, generally the steps $S_1$ and $S_2$ are continuously formed throughout the entire circumference, but may be intermittently formed.

In FIG. 1(A), the diameter (indicated by $D_1$ in FIG. 1(C)) of the edge of the rear end side step $S_1$ of the syringe barrel 1 is formed to be larger than the diameter of the edge of the front end side step $S_2$, and the tip of the inner space (inner outline) of the syringe barrel 1 is narrow.

As the piston 32, a piston is used which is formed by conical synthetic rubber (or appropriate thermoplastic elastomer), having a shape in which the rear end side (the side of the rod 31) of the cylinder is tapered, and in which the sliding surface (the side surface coming into press-contact with the inner surface of the syringe barrel 1) is not divided in the axial direction (refer to FIGS. 1(A) and 1(B)). In addition, a piston may be used in which the sliding surface of the piston 32 is divided into two stages in the axial direction. In this case, when the piston 32 moves in a sliding manner, sliding resistance changes twice for each step. As shown in FIGS. 1(A) and 1(B), in the case of using the piston in which the sliding surface is not divided in the axial direction, sliding resistance changes once for each step, and hence a doctor can easily detect the inserting distance of the piston 32 or the amount of injected medical solution.

Although it is not shown in the drawing, the surface of the piston 32 is laminated by a synthetic resin (fluorinated polymer (PTFE, ETFE)). By laminating the fluorinated resin on the conical synthetic rubber, the slidablity of the piston 32 is improved. In addition, since the fluorinated resin has excellent medical solution resistance, the fluorinated resin is desirable for the piston 32 applied to the syringe barrel 1 having prefilled medical solution.

Figure 1:
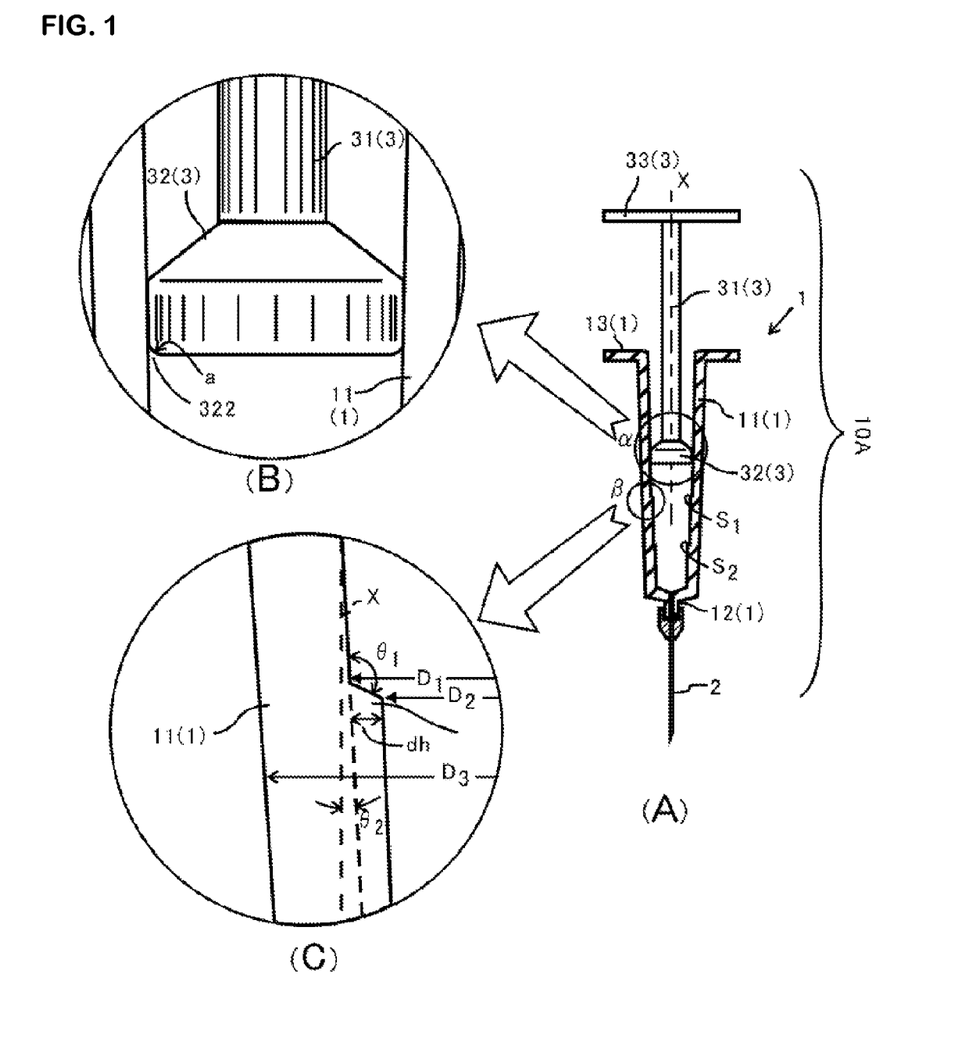
FIG. 1 is an explanatory diagram of an embodiment of a syringe barrel of the invention provided with steps and an embodiment of a syringe of the invention using the syringe barrel, where
Figure 2:
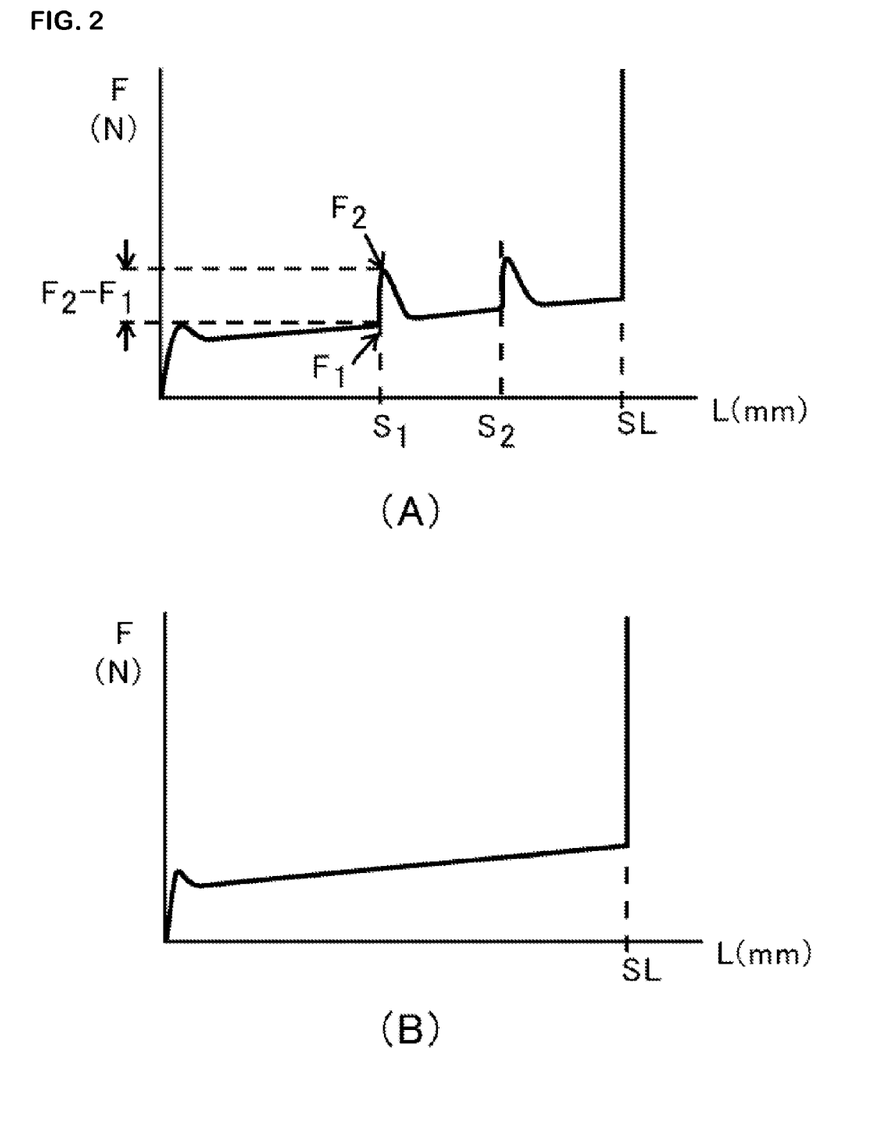
FIG. 2(A) is a diagram showing a relationship between a sliding distance of the piston and a sliding force of the syringe of FIG. 1(A)
FIG. 2(B) is a diagram showing a relationship between a sliding distance of a piston and a sliding force of a syringe of the background art of FIG. 10(A).

In addition, in the syringe 10A shown in FIG. 1(A), a relationship between a sliding force F (F is a force corresponding to the sliding resistance of the invention, and has the unit of [N]) and a sliding distance (stroke distance) L (mm) of the piston 32 upon sliding the piston 32 at a constant speed (100 mm/min) is shown in FIG. 2(A). In addition, for reference, in a syringe 200 of the background art shown in FIG. 10(A), a relationship between a sliding force F[N] and a sliding distance L (mm) of a piston 92 upon sliding the piston 92 at a constant speed (100 mm/min) is shown in FIG. 2(B).

As shown in FIG. 2(A) (or FIG. 2(B)), although a large sliding force F is needed for sliding the piston 32 (the piston 92 of FIG. 10(A)) at the slide start time (L=0 or the vicinity thereof), a small sliding force F is enough if it starts to slide. The position of the piston 32 upon inserting the piston 32 (the piston 92 of FIG. 10(A)) to the foremost end of the syringe barrel 1 is indicated by SL (mm) in FIGS. 2(A) and 2(B).

In the syringe 10A of the embodiment, as shown in FIG. 2(A), the sliding force F gradually increases in areas (the rear end side of the $S_1$, between $S_1$ and $S_2$, and the front end side of $S_2$) where the steps $S_1$ and $S_2$ do not exist (i.e., the sliding resistance gradually increases).

When the piston 32 passes through the steps $S_1$ and $S_2$, the sliding force F changes in a step shape (i.e., the sliding resistance changes in a step shape), and an operator may feel a difference in sliding resistance.

In the embodiment, the parameters to be described later are selected so that a variation in sliding resistance is within a predetermined range when the piston 32 passes through the steps $S_1$ and $S_2$ at a moving speed 100 mm/min.

The following parameters are selected so that a relationship between the value $F_2$ obtained after the change of the sliding force F and the value $F_1$ obtained before the change of the sliding force F satisfies $1.5F_1 \leq F_2 \leq 3F_1$ ... (1)

Uprising angle $\theta_1$ of step $S_1$ and $S_2$

Variation rate $(D_1-D_2)/D_2$ of height of steps $S_1$ and $S_2$

Curvature radius a of front end side corner 322 of piston 32

Shore A hardness Hs of material forming piston 32

By appropriately selecting the values of the parameters, the condition of the variation in sliding resistance (Equation (1)) can be satisfied.

In the syringe barrel 1 of FIG. 1(A), as shown in FIG. 1(C), it is desirable that the uprising angle $\theta_1$ of the steps $S_1$ and $S_2$ is equal to or more than 90 and equal to or less than 120, and in the embodiment, the uprising angle is about 110. When the uprising angle $\theta_1$ is less than 90, the corner 322 of the piston 32 may be damaged. When the uprising angle $\theta_1$ is more than 135, it is difficult for the operator to feel the difference in sliding resistance. In addition, in FIG. 1(C), the uprising angle $\theta_1$ is defined for the step $S_1$, but the uprising angle $\theta_1$ may be defined for the step $S_2$. Further, in FIG. 1(C), an angle of the inner surface of the syringe barrel 1 with respect to the center axis X (refer to FIG. 1(A)) is denoted by $\theta_2$.

It is desirable that the variation rate $(D_1-D_2)/D_2$ ($D_1$ is the diameter of the edge of the rear end side step $S_1$, and $D_2$ is the diameter of the edge of the front end side step $S_2$) of the height of the steps $S_1$ and $S_2$ is equal to or more than 0.04 and equal to or less than 0.1. In addition, in FIG. 1, $D_1$-$D_2$ is denoted by dh. When the variation rate $(D_1-D_2)/D_2$ of the height is less than 0.04, the feeling of the difference in sliding resistance is very weak. When the variation rate is more than 0.1, the possibility of damaging the piston 32 is high. In FIG. 1, $D_1$ and $D_2$ are defined for the step $S_1$, but the $D_1$ and $D_2$ may be defined for the step $S_2$. In addition, the variation rate of the height may be defined as $(D_1-D_2)/D_1$. In order to stipulate the feeling of the difference in sliding resistance, a variation $(D_1-D_2)$ in height may be used instead of the variation rate of the height. It is desirable that the variation $(D_1-D_2)$ in height is equal to or more than 0.2 mm and equal to or less than 0.5 mm When the variation in height is less than 0.2 mm, the feeling of the difference in sliding resistance is very weak. When the variation in height is more than 0.5 mm, there is a high possibility of damaging the piston 32 or a sealing function thereof.

As described above, in the case of using the piston 32 laminated with fluorinated resin, the corner 322 may be damaged, and in order to avoid such a damage, the uprising angle $\theta_1$ of the steps $S_1$ and $S_2$ is set to be equal to or more than 90 in the embodiment. Although the corner 322 may not be damaged by setting a large curvature radius a of the corner 322 of the piston 32, but when the curvature radius a is too large, it is difficult for the operator to feel the difference in sliding resistance. The value of the curvature radius a is set to be equal to or more than 0.05 and equal to or less than 0.5 mm in the embodiment. In the embodiment, as described above, it is desirable that the material of forming the piston 32 is synthetic rubber (or appropriate thermoplastic elastomer), and it is desirable that the shore A hardness Hs is equal to or more than 50 and equal to or less than 65. Generally, when the shore A hardness Hs of the piston 32 is less than 50, the sealability of the piston is damaged, or the feeling of the difference in sliding resistance is very weak. When the hardness Hs is more than 65, the sliding resistance of the piston is too high, or the possibility of damaging the piston 32 is high.

In addition, the above-described numerical values are desirably applied to the syringe of 20 mL or less (particularly, 5 mL or less). The size of the syringe is different in accordance with the capacity thereof, and the performance in use such as the sliding resistance is largely different. For example, regarding the sliding resistance, when the capacity of the syringe is 20 mL or more, the numerical value of the general sliding resistance is large. For this reason, when the sliding resistance value obtained upon passing the piston through the step increases by three times, the sliding resistance becomes a high value, which is not suitable to be handled by human force. Accordingly, generally the numerical values are appropriately designed in consideration of the purpose or function of each actual syringe.

FIGS. 3(A), 3(B), 4(A), and 4(B) are explanatory diagrams showing an injection molding process of the syringe barrel 1 shown in FIG. 1(A). An injection molding machine 4 used herein includes an outer mold 41, an upper mold 42, and an inner mold 43. In addition, for convenience of description, the injection molding machine 4 is depicted to have a configuration different from that of an actual molding machine.

FIG. 3(A) is a cross-sectional explanatory diagram showing a shape immediately before the outer mold 41 is fixed in the inner mold 43. The outer mold 41 is provided with a cavity 411, and the outline of the inner surface thereof corresponds to the outline of the outer surface of the syringe. A substantial hole 412 of a nozzle is formed at the bottom of the outer mold 41. Although it is not shown in the drawing, the outer mold 41 is a split mold including a runner 413 at the boundary face. In addition, the front end of the inner mold 43 is provided with a pin used to form the nozzle hole.

As shown in FIG. 3(B), the inner mold 43 is fixed in the cavity 411, and injection is performed. Subsequently, cooling is performed. Then, as shown in FIG. 4(A), when the upper mold 42 is opened, and the inner mold 43 and the syringe barrel 1 formed in the periphery thereof are lifted up. Then, as shown in FIG. 4(B), the syringe barrel 1 is separated from the inner mold 43. In addition, a synthetic resin (runner forming material q) remains in the runner 413 provided in the outer mold 41 (refer to FIG. 4(A)) by injecting, but the runner forming material is removed.

In the syringe 10A of FIG. 1, when the injection operation is performed, the operator such as a doctor can feel the amount of injected medial solution or the inserting distance of the piston by the difference in sliding resistance generated at the steps $S_1$ and $S_2$. In addition, since the steps $S_1$ and $S_2$ are visible from the outside, the steps also function as gradations.

Figure 5:
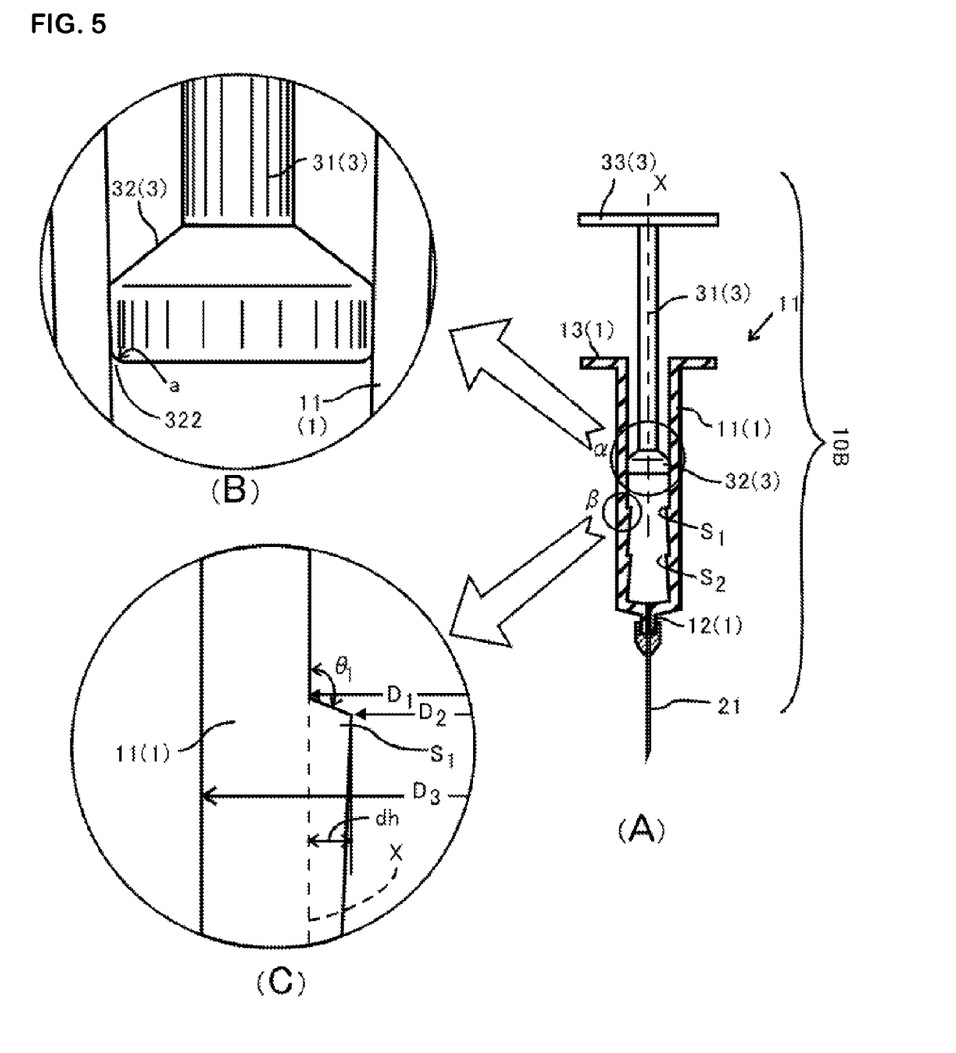
FIG. 5 is an explanatory diagram of another embodiment of the syringe barrel of the invention provided with the steps and another embodiment of the syringe of the invention using the syringe barrel, where

FIGS. 5(A), 5(B), and 5(C) are cross-sectional explanatory diagrams of another embodiment of the syringe barrel of the invention provided with the steps and another embodiment of the syringe of the invention using the syringe barrel.

A syringe 10B of FIG. 5(A) substantially has the same configuration as that of the syringe 10A of FIG. 1(A). FIG. 5(B) shows an enlarged view of the vicinity α of the piston 32 of the syringe barrel 1, and FIG. 5(C) shows an enlarged view of the vicinity β of the step $S_1$ among two steps ($S_1$ and $S_2$) of the syringe barrel 1. In FIGS. 5(B) and 5(C), the hatching of the syringe barrel 1 is omitted for convenience of description.

In FIG. 1(A), the diameter of the edge of the rear end side step $S_1$ of the syringe barrel 1 is formed to be larger than the diameter of the edge of the front end side step $S_2$. However, in FIG. 5(A), the diameter (denoted by $D_1$ in FIG. 5(C)) of the edge of the rear end side step $S_1$ is equal to the diameter of the edge of the front end side step $S_2$. That is, in the syringe barrel 1 of FIG. 5(A), the tip of the inner space is not narrow.

Figure 6:
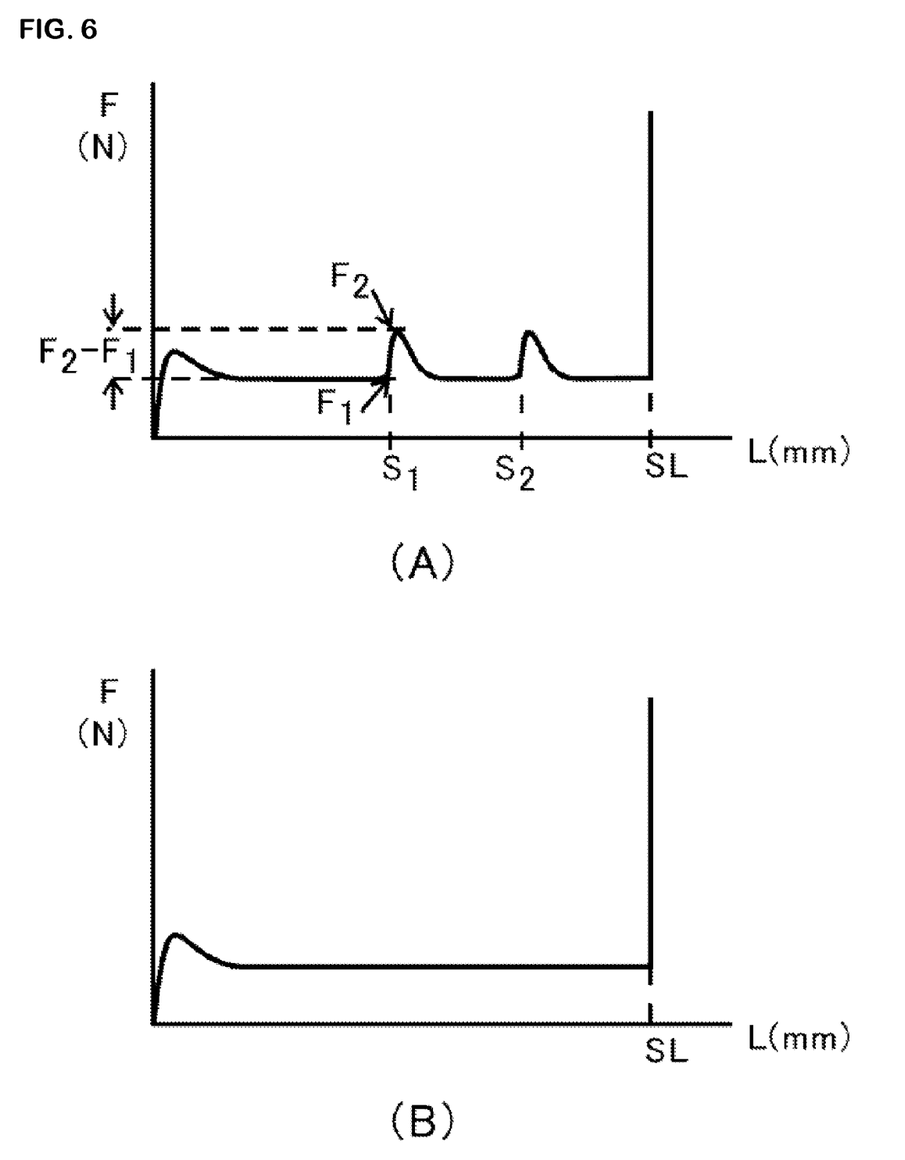
FIG. 6(A) is a diagram showing a relationship between a sliding distance of the piston and a sliding force of the syringe of FIG. 5(A)
FIG. 6(B) is a diagram showing a relationship between a sliding distance of the piston and a sliding force of the syringe of the background art of FIG. 10(A).

In the syringe 10B shown in FIG. 5(A), a relationship between the sliding force F[N] and the sliding distance L (mm) of the piston 32 upon sliding the piston 32 at a constant speed (100 mm/min) is shown in FIG. 6(A). In addition, for reference, in the syringe 200 of the background art shown in FIG. 10(B), a relationship between the sliding force F[N] and the sliding distance L (mm) of the piston 92 upon sliding the piston 92 at a constant speed (100 mm/min) is shown in FIG. 6(B).

In the syringe 10B of FIG. 5(A), when the injection operation is performed, the operator can feel the amount of injected medial solution or the inserting distance of the piston by the difference in sliding resistance generated at the steps $S_1$ and $S_2$. In addition, since the steps $S_1$ and $S_2$ are visible from the outside, the steps also function as gradations.

FIGS. 7(A), 7(B), and 7(C) are cross-sectional explanatory diagrams of an embodiment of the syringe barrel of the invention provided with an uneven portion and an embodiment of the syringe of the invention using the syringe barrel.

As shown in FIG. 7(A), a syringe 10C includes the syringe barrel 1, the needle 2, and the piston set 3. In the syringe barrel 1, the front end thereof is provided with the nozzle 12, and the rear end thereof is provided with the flange 13. The piston set 3 includes the rod 31, the piston 32, and the operational flange 33. FIG. 7(B) shows an enlarged view of the vicinity α of the piston 32 of the syringe barrel 1, and FIG. 7(C) shows an enlarged view of the vicinity β of a convex portion $CB_1$ among two convex portions ($CB_1$ and $CB_2$) of the syringe barrel 1. In FIGS. 7(B) and 7(C), the hatching of the syringe barrel 1 is omitted for convenience of description.

In the syringe 10A shown in FIG. 1(A), the inner surface is provided with the steps S1 and S2, but in the syringe 10C shown in FIG. 7(A), the inner surface is provided with the convex portions $CB_1$ and $CB_2$. In FIGS. 7(A), 7(B), and 7(C), the constituents denoted by the reference numerals are equivalent to the constituents denoted by the same reference numerals in FIGS. 1(A), 1(B), and 1(C).

In addition, in FIG. 7(A), the diameter of the rear end side convex portion $CB_1$ of the syringe barrel 1 is formed to be larger than the diameter of the front end side convex portion $CB_2$, and the tip of the inner space (inner outline) of the syringe barrel 1 is narrow.

In the embodiment, the parameters to be described later are selected so that a variation in sliding resistance is within a predetermined range when the piston 32 passes through the convex portions $CB_1$ and $CB_2$ at a moving speed 100 mm/min. That is, assuming that a value of the sliding force F after a change is denoted by $F_2$, and a value of the sliding force F before a change is denoted by $F_1$, the following parameters are selected in order to satisfy $1.5F_1 \leq F_2 \leq 3F_1$.

Curvature radius b of convex portions $CB_1$ and $CB_2$
Variation rate $(D_1-D_2)/D_2$ of height of convex portions $CB_1$ and $CB_2$
Curvature radius a of front end side corner 322 of piston 32
Shore hardness Hs of material forming piston 32

By appropriately selecting the values of the parameters, the condition of the variation rate of the sliding resistance can be satisfied.

Figure 8:
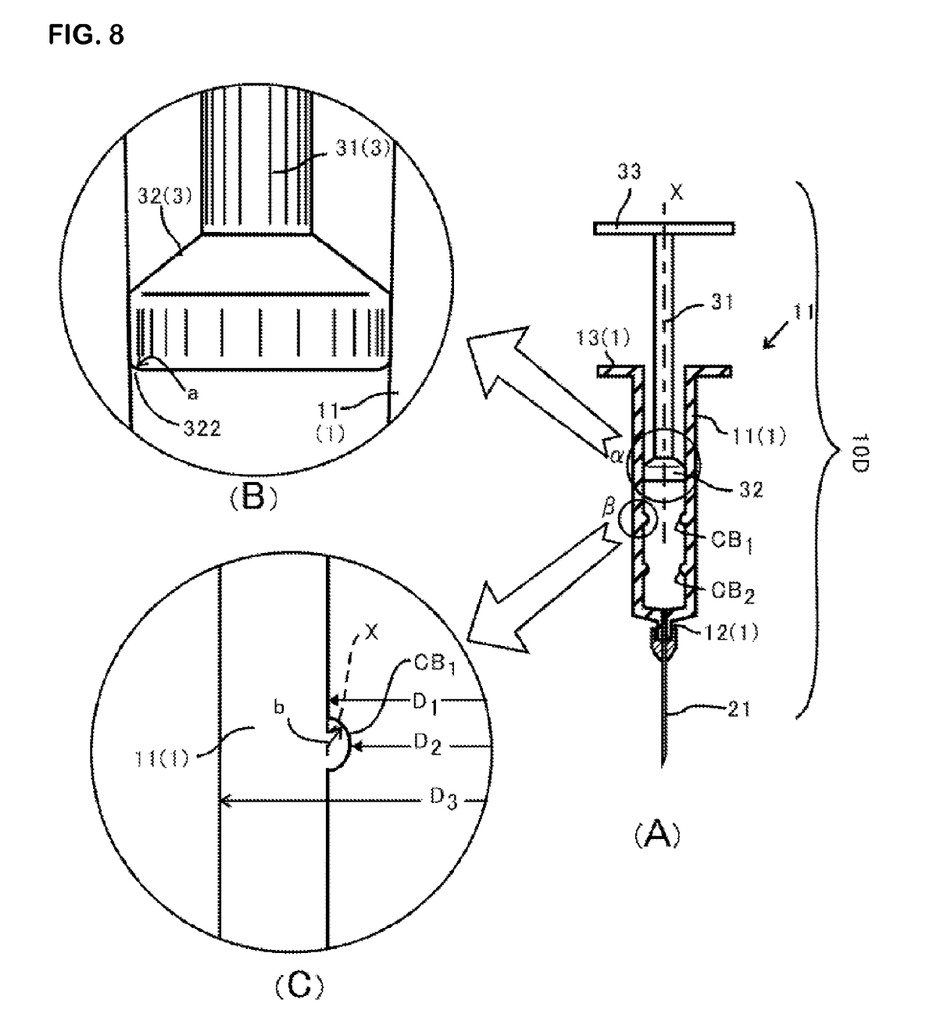
FIG. 8 is an explanatory diagram of another embodiment of the syringe barrel of the invention provided with the uneven portion and another embodiment of the syringe of the invention using the syringe barrel, where

FIGS. 8(A), 8(B), and 8(C) are cross-sectional explanatory diagrams of another embodiment of the syringe barrel of the invention provided with the uneven portion and another embodiment of the syringe of the invention using the syringe barrel.

A syringe 10D of FIG. 8(A) substantially has the same configuration as that of the syringe 10C of FIG. 7(A). FIG. 8(B) shows an enlarged view of the vicinity α of the piston 32 of the syringe barrel 1, and FIG. 8(C) shows an enlarged view of the vicinity β of the convex portion $CB_1$ among two convex portions ($CB_1$ and $CB_2$) of the syringe barrel 1. In FIGS. 8(B) and 8(C), the hatching of the syringe barrel 1 is omitted for convenience of description.

In FIG. 7(A), the inner diameter of the rear end side convex portion $CB_1$ of the syringe barrel 1 is set to be larger than the inner diameter of the front end side convex portion $CB_2$ (i.e., the tip of the inner outline is narrow), However, in FIG. 8(A), the inner diameter of the rear end side convex portion $CB_1$ is set to be equal to the inner diameter of the front end side convex portion $CB_2$ (i.e., the diameter of the inner outline is constant).

Figure 9:
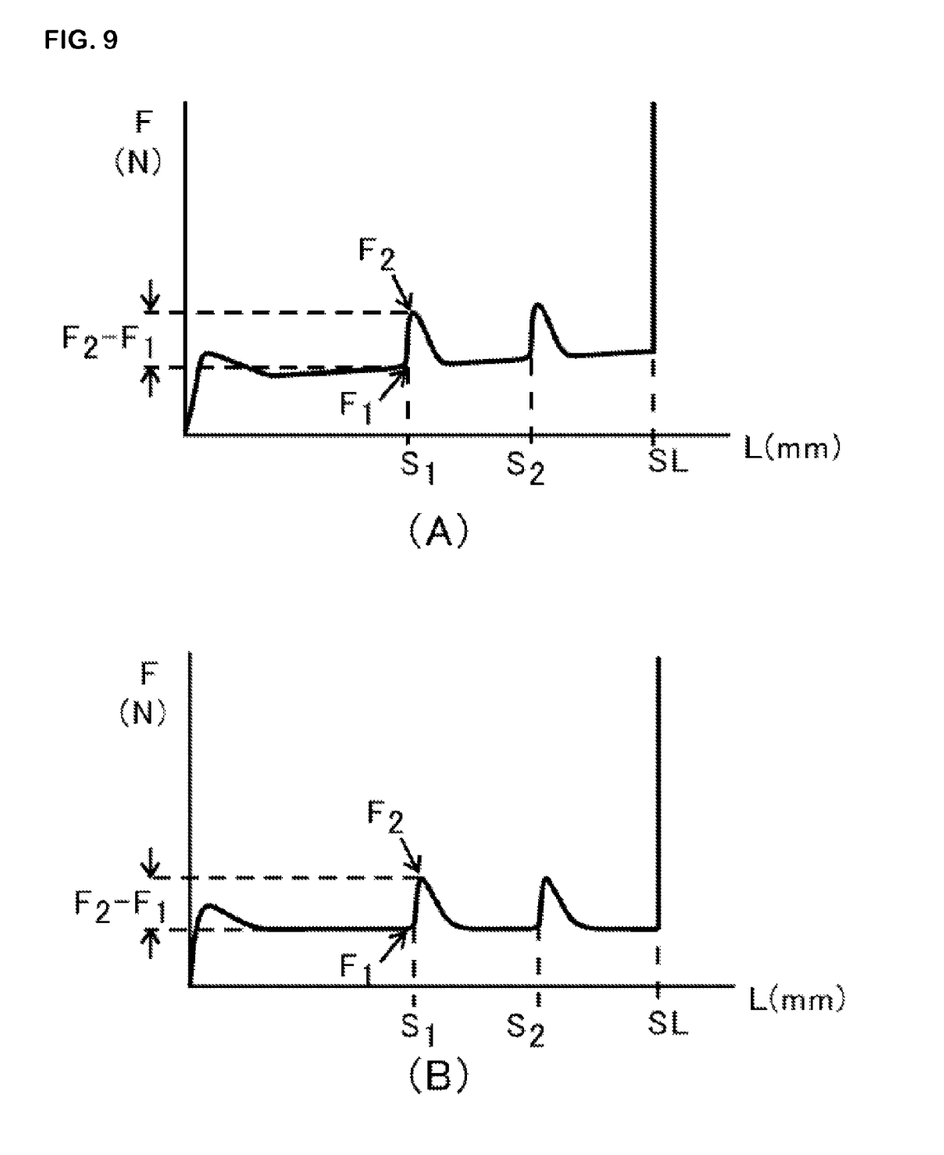
FIG. 9(A) is a diagram showing a relationship between a sliding distance of the piston and a sliding force of the syringe of FIG. 7(A)
FIG. 9(B) is a diagram showing a relationship between a sliding distance of the piston and a sliding force of the syringe of FIG. 8(A).

In the syringe 10C shown in FIG. 7(A), a relationship between the sliding force F and the sliding distance L (mm) of the piston 32 upon sliding the piston 32 at a constant speed (100 mm/min) is shown in FIG. 9(A). Also, in the syringe 10D shown in FIG. 8(A), a relationship between the sliding force F and the sliding distance L (mm) of the piston 32 upon sliding the piston 32 in the same manner as described above is shown in FIG. 9(B).

In the syringe 10C of FIG. 7(A) and the syringe 10D of FIG. 8(A), when the injection operation is performed, the operator can feel the amount of injected medical solution or the inserting distance of the piston by the difference in sliding resistance generated at the convex portions $CB_1$ and $CB_2$. In addition, since the convex portions $CB_1$ and $CB_2$ are visible from the outside, the convex portions function as gradations.

In the embodiments shown in FIGS. 1(A), 1(B), 1(C), 5(A), 5(B), and 5(C), the steps $S_1$ and $S_2$ uprightly formed toward the front end, and have the edges formed along the circumferential direction. However, for example, in the case where the syringe is used in a direction of pulling the piston for the purpose of collecting blood, the steps $S_1$ and $S_2$ may be uprightly formed from the front end to the rear end, and may have the edges formed along the circumferential direction.

In addition, although it is not shown in the drawings, as another embodiment of the invention, there is a syringe which has one edge provided only in the general gradation of the injection amount. Generally, in the syringe, in order to discharge air inside the syringe barrel to the outside, an operation of discharging a part of medical solution from the syringe is performed before injecting medical solution into a human body. Accordingly, in the syringe, in order to inject a dosage of medical solution, the amount of medical solution is checked and additional medical solution is discharged. This operation is performed immediately before the injection operation, and is performed by checking the gradation. For this reason, some time is necessary, and the precision is dependent on the doctor.

By using the syringe of the embodiment, when the doctor presses the rod to a position where the sliding resistance increases by checking a discharge state of air inside the syringe, an extra amount of medical solution can be discharged, and hence the preparation for the injection operation can be completed with satisfactory precision and promptness.

The invention claimed is:

1. A variable resistance syringe comprising:
a piston set including,
    a piston head,
    a piston rod connected at one end to said piston head, and
    an operational flange connected to said piston rod at the other end thereof; and
a syringe barrel operable to receive said piston head at a first end thereof and to dispense a fluid from said syringe barrel from a second end thereof,
    said syringe barrel having a fluid capacity of approximately twenty millimeters or less,
    said syringe barrel having a first interior projection extending laterally into the interior of said syringe barrel, and
    said syringe barrel having a second interior projection extending laterally into the interior of said syringe barrel and being axially spaced from said first interior projection downstream of said first interior projection within said syringe barrel,
    said first interior projection within said syringe barrel offering a sliding resistance force to travel of said piston head within said syringe barrel of a magnitude of F1 and said second interior projection within said syringe barrel offering a sliding resistance force to travel of said piston head within said syringe barrel of a magnitude of F2, and
    the relative magnitude of the forces F1 and F2 within the syringe barrel when the piston head is traveling at a speed of approximately one hundred millimeters per minute satisfies by the following relationship:

$1.5 F1 < F2 < 3 F1$.

2. A variable resistance syringe as defined in claim 1 wherein said first and second interior projections each comprises:
    a peripheral convex protrusion extending interiorly within said syringe barrel.

3. A variable resistance syringe as defined in claim 1 wherein said first and second interior projections each comprises:
    a peripheral step extending interiorly within said syringe barrel and each step extending from an interior wall surface of said syringe barrel with a leading angle "$\Theta$" where the leading angle "$\Theta$" is greater that ninety degrees and less than or equal to one hundred and twenty degrees.

4. A variable resistance syringe as defined in claim 3 wherein:
    said first and second interior projections extend interiorly within said syringe barrel with the interior diameter of the barrel immediately preceding a step being D1 and the interior diameter of the barrel with the step being D2 and the relationship of the diameter of D1 to D2 being approximately:

$0.04 < (D1-D2)/D2 < 0.1$.

5. A variable resistance syringe as defined in claim 4 wherein:
    a leading peripheral edge of said piston head has a curvature radius "$\phi$" greater than or equal to 0.05 millimeters and less than or equal to 0.5 millimeters.

6. A variable resistance syringe as defined in claim 5 wherein:
    said piston head is composed of a material with a shore hardness of greater than or equal to 50 and less than or equal to 65.

7. A variable resistance syringe as defined in claim 3 wherein:
    said first and second interior projections extend interiorly within said syringe barrel with the interior diameter of the barrel immediately preceding a step being D1 and the interior diameter of the barrel with the step being D2 and the diameter of D1 and D2 satisfies:

$0.2 < (D1-D2) < 0.5$.

8. A variable resistance syringe as defined in claim 7 wherein:
    a leading peripheral edge of said piston head has a curvature radius "$\phi$" greater than or equal to 0.05 millimeters and less than or equal to 0.5 millimeters.

9. A variable resistance syringe as defined in claim 8 wherein:
    said piston head is composed of a material with a shore hardness of greater than or equal to 50 and less than or equal to 65.

* * * * *